United States Patent [19]

Tinois et al.

[11] Patent Number: 5,654,135
[45] Date of Patent: Aug. 5, 1997

[54] BIOMATERIAL BASED ON COLLAGEN AND ITS APPLICATION

[75] Inventors: Estelle Tinois, Tassin La Demi-Lune; Jérôme Tiollier, Lyons; Henri Dumas, Lyons; Michel Tardy, Lyons, all of France

[73] Assignees: Imedex, société anonyme; Pasteur Merieux Sérums et Vaccins, société anonyme, both of Lyons, France

[21] Appl. No.: 491,260

[22] Filed: Jun. 19, 1995

Related U.S. Application Data

[63] Continuation of Ser. No. 173,873, Dec. 27, 1993, abandoned, which is a continuation of Ser. No. 856,218, May 14, 1992, abandoned.

[30] Foreign Application Priority Data

Oct. 2, 1990 [FR] France ................... 90 12135

[51] Int. Cl.$^6$ .................. A61K 35/36; C12N 5/06; C12N 5/08; A61F 2/10
[52] U.S. Cl. .................. 435/1.1; 424/93.1; 424/93.3; 424/93.7; 435/240.1; 435/240.2; 435/240.21; 435/240.23; 435/240.243; 530/356; 530/402; 623/15
[58] Field of Search ................... 424/93.1, 93.3, 424/93.7; 435/1.1, 204.1, 240.2, 240.21, 240.23, 240.243; 530/356, 402; 623/15

[56] References Cited

FOREIGN PATENT DOCUMENTS 8903392  4/1989  WIPO.
8908467  9/1989  WIPO.

OTHER PUBLICATIONS

Bosca et al., J. Inv. Derm., vol. 91, pp. 136–141, 1988.

Wilke et al; "Human keratinocytes adhere to a unique heparin–binding peptide sequence within the triple helical region of type IV collagen"; Journal of Investigative Dermatology, vol. 95, No. 3, pp. 264–270, Sep. 1990.

Tinois et al; "Growth and differentiation of human keratinocytes on extracellular matrix"; Biological Abstracts, vol. 84, No. 8, pp. AB–565, Abrege No. 88152, 1987.

Tinois et al; "In vitro and post–transplantation differentiation of human keratinocytes grown on the human . . . "; Experimental Cell Research, vol. 193, pp. 310–319, 1991.

*Primary Examiner*—Ronald B. Schwadron
*Attorney, Agent, or Firm*—Larson & Taylor

[57] ABSTRACT

Biomaterial based on collagen comprises, intimately associated, a support forming a dermal substitute, said support comprising a layer based on type IV collagen and an epidermal epithelium having differentiated cells obtained by growing epidermal cells on said support.

5 Claims, No Drawings

BIOMATERIAL BASED ON COLLAGEN AND ITS APPLICATION

This application is a continuation of application Ser. No. 08/173,873 filed Dec. 27, 1993 (now abandoned) which is a continuation of Ser. No. 07/856,218 filed May 14, 1992 (now abandoned).

The present invention relates to a biomaterial based on collagen and applications thereof.

In the last twenty years, major advances have been made in the epidermal cell culture domaine. These advances have permitted the growth of an increasing number of cells (bibliographic references 1 and 2) and have provided important insight into the factors which regulate growth and the terminal differentiation of the epidermis. Different systems have been developed permitting the modulation of both growth and differentiation (2, 3, 4). In order to further study the regulation of these biological phenomena with a view to studying dermal-epidermal interactions and reconstructing a skin-like tissue, cells have been grown on more or less complex dermal substitutes (references 5 to 13). As keratinocytes poorly anchor onto the dermal substitute, the formation of the basement membrane in vitro has been the subject of many works. The only published reports on the reformation of an almost complete basement membrane by dispersed human keratinocytes grown on collagen have described long-term cultures (40-60 days) (14, 15). Authors have reported the role of type IV collagen in the culture of keratinocytes (22, 23, 24).

Further, there has already been realized (EP-A-0,357, 755) a visceral surgery patch formed of two intimately associated superposed layers of collagen, namely a porous layer of fibrous collagen and a film of collagen, it being possible for the collagen to be in particular of the type III+I or of the type IV.

An object of the present invention is to provide a biomaterial comprising differentiated epidermal cells and in particular a biomaterial of this type the structure of which is substantially close to that of the skin.

Another object of the invention is to provide a biomaterial of use in pharmacology, toxicology and cosmetology and/or for the protection of wounds, burns or for cicatrization.

The applicant has found surprisingly that a type IV collagen matrix permitted the culture of epidermal cells, in particular keratinocytes, by acting as a support or dermal substitute and obtaining very rapidly a biomaterial the general structure of which is close to that of the skin with, in particular, formation of that which can be likened to a basement membrane and horny cells.

The invention therefore provides a biomaterial based on collagen, comprising, intimately associated, a support or dermal substitute based on type IV collagen and an epidermal epithelium having differentiated cells obtained by the growth of epidermal cells on said support or substitute.

Advantageously, the support or dermal substitute may further comprise a sublayer of type I+III collagen in the form of a porous network.

The collagens employed may be cross-linked or native and may be an appropriate mixture of native collagen and cross-linked collagen.

The type IV collagen may be in particular of placenta origin and prepared in accordance with the teaching of patent EP-A-0,214,035.

Preferably, the epidermal cells of colonisation are keratinocytes, in particular adult normal human keratinocytes (ANHK).

The epithelium of this biomaterial has in particular the following characteristics:

a) after 6 days of culture, a good reconstitution of the anchorage structures in the region of the dermal-epidermal junction: many well-individualized hemidesmosomes (anchorage plate with tonofilaments inserted therein, dense sub-basal plate, anchoring filaments) in a deposition in the form of an even band of extracellular material between the surface of the type IV collagen and the plasmal membrane resembling a lamina densa.

b) 3 cell compartments:
a gasement cell seating,
a plurality of intermediate cell seatings interconnected by desmosomes, containing granules of keratohyalin for the most superficial thereof,
a horny stratum.

The invention also provides the application of this biomaterial in pharmacological, toxicological or cosmetological tests, in particular in the form of an in vitro evaluation kit.

The invention further provides the application of this biomaterial in the protection/cicatrization of wounds and burns.

The invention will now be described in more detail with the aid of a process for preparing a biomaterial according to the invention and in vitro and in vivo tests.

Preparation of the Collagens

The preparation of native or oxidized type IV collagen is carried out in accordance with the process described in the patent EP-A-0,214,035.

The type I+III collagens may be prepared by any known process.

Preparation of the Dermal Substitute

The dermal substitute comprises lyophilized and oxidized I+III type collagens covered by a film of a mixture of type IV collagen and oxidized type IV collagen. To prepare the dermal substitute, a periodic acid solution (0.002M final concentration) was added to a 10 mg/ml solution of type I and type III collagens in 0.01N hydrochloric acid. The oxidized collagens were recovered by phosphate precipitation ($Na_2HPO_4$). The precipitate was washed several times with phosphate buffer ($Na_2HPO_4$) and recovered by filtration on Nylon linen. The product obtained was put into the form of sheets, lyophilized and compressed. The oxidation induced by the periodic acid led to the formation of a cross-linked collagen matrix (U.S. Pat. No. 4,931,546).

A solution of oxidized type IV (IVox) collagen was made by adding periodic acid (0.02M final concentration) to a 20 mg/ml solution of type IV collagen in 0.01N hydrochloric acid. After 2 hours of incubation, the type IVox collagen was dialyzed against 0.01N hydrochloric acid.

A mixture of 10 mg/ml of a type IV collagen preparation and 10 mg/ml of an oxidized type IV collagen (4:1) (IV/IVox) was laid on the surface of the type I+III collagen sponge and then dried. The sterilization of the dermal substitute was carried out by (25 kgray) gamma-irradiation.

Culture of ANHK (Adult Normal Human Keratinocytes)

Human epidermal cell suspensions were prepared by standard trypsinization procedures from normal adult skin specimens removed during plastic surgery operations. The cells were grown on gamma-irradiated 3T3 feeder cell layers in accordance with H. Green's method (1).

The culture medium was DMEM (Gibco Laboratories, Grand Island, N.Y. USA) and HAM F12 (Gibco) (3:1) supplemented with 10% foetal calf serum (Boehringer Mannheim, Meylan, France), $1.8 \times 10^{-4}$M adenine, 5 µg/ml insulin, $2 \times 10^{-9}$M triiodothyronine, 5 µg/ml transferrin, 0.4 µg/ml hydrocortisone, $10^{-10}$M cholera toxin and 10 µg/ml epidermal growth factor, all purchased from SIGMA, USA (complete medium). At confluence, the keratinocytes were trypsinized and stored in liquid nitrogen. Circular samples of dermal substitute, 1.6 cm in diameter, were placed in 24-well-culture plates (Falcon) and pressed to make them adhere to the plastics material. Keratinocytes in suspension were directly seeded onto these samples and put in contact with a culture medium ($5 \times 10^4$ cells/$cm^2$ were seeded so as to attain the confluence in 4 days). Cultures were incubated at 37° C. in a 5% $CO_2$ atmosphere and the culture medium was changed every two days. When the epidermal cell confluence was attained, the skin substitute obtained was removed for a microscopic examination or for transplantation onto mice. Some dermal substitutes were placed, 5 days after plating, on steel grids to bring the keratinocyte culture to the air-liquid interface. The cells were then air-exposed and fed through the dermal substitute.

The upper part of the dermal substitute is a type IV/IVox collagen layer. In order to investigate the ability of the biomaterial to permit epidermal cell growth, ANHK were cultured onto the type IV/IVox collagen layer of the same type made up in 6-well-plates so as to permit a direct microscopic observation. The cells were seeded in suspension onto the layers in a complete medium or in a serum-free medium. The serum-free medium was DMEM and HAM F12 (1:1) (Gibco) supplemented with 0.5 µg/ml hydrocortisone, 5 µg/ml insulin, $3 \times 10^{-8}$M selenite (SIGMA), 5 µg/ml transferrin, 1 mg/ml albumine (Institut Mérieux, Lyon, France), 5 µg/ml fibronectin (Institut Mérieux). High seeding densities: $10^5$, $5 \times 10^4$, $3 \times 10^4$ cells/$cm^2$ were tested in complete medium and a low seeding density, $8 \times 10^3$ cells/$cm^2$, in the serum-free medium.

Epidermal Cell Differentiation

For histology, the samples were fixed in Bouin's fixative medium, dehydrated in alcohol and embedded in paraffin and methacrylate. Sections were stained with HES (hematoxyline-eosine-saffron). Immunohistochemical studies were carried out either on de-paraffinized or frozen sections, by using an avidin-biotin-alkaline phosphatase or by indirect immunofluorescence.

Epidermal differentiation was investigated by using 3 monoclonal antibodies: anti-keratin KL1 (Immunotech, Marseille, France); AKH1, a monoclonal antibody to human profilaggrin/filaggrin (Biomedical Tech. Inc., Soughton, USA), and a rabbit polyclonal antibody to involucrin (Biomedical Tech.). A mouse monoclonal antibody to beta-2 microglobulin (Immunotech) was used as a marker of human class I antigen (16 and 17).

For transmission electron microscopy, samples were fixed in 1% glutaraldehyde, 0.5% paraformaldehyde, 0.1M phosphate buffer, prefixed in 1% osmium tetroxide, dehydrated in alcohol and embedded in an epoxy medium. Ultrathin sections were observed and photographed with a JEOL 1200 EX transmission electron microscope (18).

Transplantation to an Athymic Mouse

The grafting technique comes from that previously described in the bibliographic reference 19. Briefly, 17 congenitally athymic mice (Swiss nu-nu, Iffa Credo, Lyon, France) (6–10 weeks old) were anaesthetized using sodium pentobarbital, and a circular graft bed, 1.5 cm in diameter, was prepared on the dorso-lateral side of each animal by delicately removing the epidermis and the dermis, leaving the vascularization tissue on the fascia.

The graft, with its edges placed under the adjacent skin of the mouse, is overlaid with a vaseline-impregnated gauze and a capsule of plastics material (for 4 mice out of 17) maintained in place by 4 cross-formed loose sutures and protected by a bandage. For 7 other mice, the capsules of plastics material are omitted and the grafts are maintained in place and protected by a compressive bandage. Alternatively, for the 6 remaining mice, the capsules of plastics material are replaced by a silicone transplantation chamber (Renner GmbH, Darmstadt, RFA) which was placed on the graft and which is maintained in place with 9 mm clips. After 14, 20 or 30 days, the bandage, the capsule and the gauze were removed and the grafts were surgically excised and processed for light or electron microscopy.

Study of the Basement Membrane

The formation of the basement membrane was studied by indirect immunofluorescence on frozen sections and by transmission electron microscopy.

Antibodies to laminin (institut Pasteur), antibodies to type IV collagen (Institut Pasteur) or mouse monoclonal antibodies to human type IV collagen (HEYL) and the serum from patients with Bullous Pemphigoid (BP) were used to detect the three components of the dermal-epidermal junction.

RESULTS

The Dermal Substitute

The dermal substitute is composed of a porous (pore diameter-50 to 100 microns) fibrous type I+III collagen layer of 400 microns thick overlaid by a dense type IV/IVox collagen film of 10 to 20 microns thick.

When overlaid with multilayered epithelium, the substitute may be easily handled without any support. By indirect immunofluorescence, the antibody to type IV collagen showed a thin layer on the surface of the type I+III layer and thin filaments included in the type I+III layer, demonstrating that the type IV/IVox collagen had slightly penetrated into the type I+III layer.

In Vitro ANHK Growth and Differentiation

The ANHK rapidly attaches to the collagen, spreads, and divides to form a confluent epithelium. Confluence is obtained in 3, 4 and 5 days when $10^5$, $5 \times 10^4$ and $3 \times 10^4$ cells/$cm^2$ are respectively seeded. In a serum-free culture medium, a seeding density of $8 \times 10^3$ cells/cm allows confluency in 13 days.

Using histological and electron microscopic methods, it can be seen that the differentiation of the epidermal cells occurs from day 6 to day 25 after plating. Histological examination after 14 days in culture, shows a multilayered epithelial sheet composed of a well-organized basal cell layer and several suprabasal cell layers with more flattened and anucleated cells. Sparse keratohyalin granules are observed in the cytoplasm of the cells beneath the anucleated cell layers. When the cultures are exposed to the air, a thick horny layer is observed. Parakeratosis is occasionally observed.

At day 6, a basal cell layer composed of small cuboidal cells with a distinct nucleus, cytoplasmic organelles, intermediate filaments and tonofilaments, may be seen by electron microscopy. This layer is overlaid with suprabasal layers of more elongated cells which contain numerous organelles and intermediate filaments but no keratohyalin granules. The stratification then increases with the age of the culture. The cell layers are closely associated with well-structured desmosomes and narrow inter-cellular spaces. The keratohyalin granules are sparse, have a round shape and are observed in the upper-intermediate cell layers. Thereafter, the stratification does not significantly increase but anucleated and somewhat desquamating cells may be observed.

In Vivo ANHK Differentiation

A well-stratified epidermis is observed only when the grafts have been maintained under graft chambers of plastics or silicone material which inhibit murine epidermal cell migration. At day 14, the type I+III collagen layer of the dermal substitute starts to be infiltrated by inflammatory and fibroblast cells. At day 30, the type I+III collagen fibres are only partly present, colonized by numerous fibroblasts and a few mononuclear cells. The degradation of the type I+III collagen layer leads in a heterogeneous manner to almost intact collagen fibres in some areas or to a reorganized tissue containing sparse human collagen fibres in others. The type IV/IVox collagen layer remains substantially intact and non-infiltrated. Thus, the type IV/IVox collagen seems resistant to degradation in these occlusive conditions. When the dermal substitute is grafted under non-occlusive conditions, its degradation is more rapid. After grafting, the epithelium develops both a granular and a horny layer grafted epidermis i. The grafted epidermis is not hypertrophic as commonly described when cultured epithelium or skin-substitute are grafted (20 and 21).

Two weeks after grafting, abundant keratohyalin granules in the upper viable layer and a stratum corneum with a mild orthokeratosis are observed. At day 20, the beta-2 microglobulin is expressed in the basal cell layer and only weakly in a few suprabasal layers. At day 30, the basal cell and suprabasal cell layers are strongly labelled.

At day 14, the staining obtained with the KL1 antibody was observed for all the epidermal layers. The basal cell layer starts to be partially negative on day 20. The profilaggrin/filaggrin labelling is limited to the granular layer, as observed in normal human skin. Involucrin expression is in superbasal position on day 14, 20 and 30. Nevertheless, at day 30 and 55, in large areas this expression is restricted to the intermediate, upper Malpighian layers and granular layers on day 30.

Study of the Dermal-Epidermal Junction in Vitro

Electronic microscopy shows numerous hemidesmosome-like structures at the junction between the type IV/IVox collagen film and the basal cells as soon as the day 6 after plating. The dermal-epidermal junction is linear without ridges. There is observed an intracellular electron-dense plaque along the basal cell membrane in which are inserted intermediate filaments and a subbasal dense layer. Anchoring filaments may be distinguished. The surface of the film appears as a dense line and an electron-dense band resembling lamina densa seems to overlay it. This resembles a dermal-epidermal junction in the skin of a human foetus at an intermediate stage of development.

By immunofluorescence, the BP antigen is expressed from day 6 in culture, whereas the laminin which is not detectable at this stage may be detected from day 12. Both antigens' labelling are observed on the basal side of basal cells in the form of a discontinuous fluorescence. The immunofluorescence reaction using the antibody to type IV collagen shows a fluorescence on the whole thickness of the type IV/IVox collagen film.

In Vivo

At day 30 and day 55 after transplantation, the fine structure of the basement membrane is more clearly seen than in culture in vitro since the IV/IVox type collagen appears less dense. Numerous well-differentiated hemidesmosomes and a lamina densa are distinguished. In some areas, the type IV/IVox collagen layer seems to be partly degraded by the epidermal cells. In these areas, at day 30, fibrils reminiscent of anchoring fibrils may be seen under the lamina densa. At day 55, the connective tissue beneath the lamina densa is better organised and the anchoring fibrils are well-structured. By light microscopy, the dermalepidermal junction appears slightly undulating and, by electron microscopy, the dermal-epidermal interface of the basal cells form an undulating plasma membrane in its basal portion.

The quality of the epidermis obtained permits applying the material to toxicological, pharmacological and cosmetological evaluation tests in accordance with the usual procedures employed in biopsies of the human and anima

BIBLIOGRAPHICAL REFERENCES

1. Green H., Kehinde O. & Thomas J., Proc. Natl. Acad. Sc., USA 76 (1979) 5665
2. Boyce S. & Ham R G., J. Invest. Dermatol. 81 (1983) 33s
3. Hennings H., Michael D., Cheng C., Steward S., Holbrook K. & Yuspa S H., Cell 19 (1980) 245
4. Asselineau D., Bernard B., Bailly C. & Darmon M. Exp. Cell. Res. 159 (1985) 536
5. Bell E., Sher S., Hull B., Merill C., Rosen S., Chamson A., Asselineau D., Dubertret L., Coulomb B., Lapiere C., Nusgens B. & Neveux Y., J. Invest. Dermatol. 81 (1983) 2s
6. Coulomb B., Saiag G P., Bell E., Breitburd F., Lebreton C., Heslan M. & Dubertret T., Br. J. Dermatol. 114 (1986) 91
7. Prunieras M., Regnier M. & Woodley D., J. Invest. Dermatol. 81 (1983) 28s
8. Regnier M., Desbas C., Bailly C. & Darmon M., In vitro 24 (1988) 625
9. Regnier M. & Darmon M., In vitro, 25 (1989) 1000
10. Lenoir M-C., Bernard B., Pautrat G., Darmon M. & Shroot B., Dev. Biol. 130 (1988) 610
11. Freeman A E., Igel H J., Herman B J & Kleinfeld K L., In vitro 12 (1976) 352
12. Yannas I V. & Burke J F., J. Biomed. Mater. Res. 14 (1980) 65
13. Boyce S. & Hansbrough J., Surgery 103 (1988) 421
14. Hirone T. & Taniguchi S., Cur. Prob. Dermatol. 10 (1980) 159
15. Chamson A., Germain N., Claudy A., Perier C. & Frey J., Arch. Dermatol. 281 (1989) 267
16. Forsum U. & Tjemlund U M., Acta Venereol (Stockh) 57 (1977) 121
17. Mauduit G., Vincent C L., Gielen V., Faure M., Demiden A. & Thivolet J., Tissue antigens 29 (1987) 65
18. Garrone R. & Tiollier J., dans Bienvenu, Grimaud, Laurent, Walterde, Gruyter (Eds), Marker proteins, vol. 3 1986. pp 357-361
19. Tinois E., Faure M., Kanitakis J., Ramirez-Bosca A., Nguyen C., Tardy M., Tayot J L. & Thivolet J., Epithelia 1(1987) 141

20. Faure M., Mauduit G., Schmitt D., Kanitakis J., Demidem A. & Thivolet J., Br. J. Dermatol. 116 (1987) 161
21. Ramirez-Bosca A., Tinois E., Faure M., Kanitakis J., Roche P. & Thivolet J., J. Invest. Dermatol. 91 (1988) 36
22. Murray J C., Stingl G., Kleinman H K., Martin G R. & Katz S I., J. Cell. Biol, 80 (1979) 197
23. Kleinman H K., Murray J C., Mc Goodwin E B. & Martin G R., J. Invest. Dermatol. 71 (1978) 9
24. Woodley D., Kimberly C. & O'Keefe J., J. Invest. Dermatol. 94 (1990) 139.

We claim:

1. Biomaterial based on collagen characterized in that it consists essentially of, intimately associated, a support forming a dermal substitute, said support consisting of a layer based on type IV collagen and a multilayered differentiated epithelium obtained by growing epidermal cells in vitro, harvesting them and then culturing them on said support until stratification with cell differentiation occurs.

2. Biomaterial according to claim 1, characterized in that the epidermal cells are keratinocytes.

3. Biomaterial based on collagen characterized in that it consists essentially of, intimately associated, a support forming a dermal substitute, said support consisting of a layer based on type IV collagen associated with a sublayer consisting of type I+III collagens, and a multilayered differentiated epithelium obtained by growing epidermal cells in vitro, harvesting them and then culturing them on said support until stratification with cell differentiation occurs.

4. Biomaterial according to claim 1 or claim 3, characterized in that the collagen is native or cross-linked collagen or a mixture of native collagen and cross-linked collagen.

5. In a kit comprising a biomaterial for in vitro toxicological pharmacological or cosmetological tests, the improvement wherein said biomaterial is the biomaterial of claim 1 or claim 3.

* * * * *